United States Patent [19]

Noyori et al.

[11] Patent Number: 4,895,979
[45] Date of Patent: Jan. 23, 1990

[54] PROCESS FOR PREPARING CARNITINE

[75] Inventors: Ryoji Noyori; Masato Kitamura, both of Aichi; Takeshi Ohkuma, Gumma; Hidenori Kumobayashi, Kanagawa, all of Japan

[73] Assignee: Takasago International Corporation, Tokyo, Japan

[21] Appl. No.: 313,007

[22] Filed: Feb. 21, 1989

[30] Foreign Application Priority Data

Feb. 19, 1988 [JP] Japan .................................. 63-37032

[51] Int. Cl.$^4$ ..................... C07C 51/09; C07C 53/124
[52] U.S. Cl. ..................................... 562/567; 560/184
[58] Field of Search .......................... 562/567; 560/184

[56] References Cited

U.S. PATENT DOCUMENTS

| | | | |
|---|---|---|---|
| 3,135,788 | 6/1964 | Noguchi et al. | 562/567 |
| 3,151,149 | 9/1964 | Strack et al. | 562/567 |
| 3,462,485 | 8/1969 | Binon et al. | 562/567 |
| 3,969,406 | 7/1976 | Tenud | 562/567 |
| 4,018,821 | 4/1977 | Tenud | 562/567 |
| 4,021,480 | 5/1977 | Tenud | 562/567 |
| 4,413,142 | 11/1983 | Fiorini et al. | 562/567 |
| 4,664,852 | 5/1987 | Casati et al. | 560/184 |

FOREIGN PATENT DOCUMENTS

| | | | |
|---|---|---|---|
| 0167115 | 1/1986 | European Pat. Off. | 562/567 |
| 0161953 | 8/1985 | Japan | 562/567 |
| 2132614 | 7/1984 | United Kingdom | 560/184 |

Primary Examiner—J. E. Evans
Attorney, Agent, or Firm—Sughrue, Mion, Zinn, Macpeak & Seas

[57] ABSTRACT

A process for preparing carnitine which comprises asymmetrically hydrogenating a γ-halogeno-β-keto ester represented by formula (I):

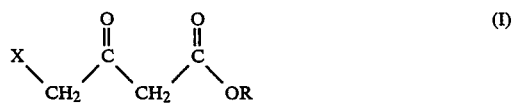

wherein X represents a chlorine atom or a bromine atom; and R represents a lower alkyl group, in the presence of a ruthenium-optically active phosphine complex represented by formula (II), (III) or (IV):

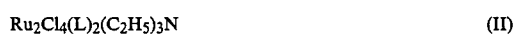
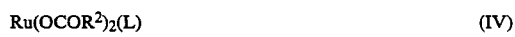
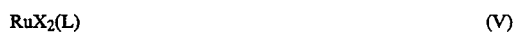

wherein L represents 2,2'-bis(di-p-R$^1$-phenylphosphino)- 1,1'-binaphthyl of formula (III):

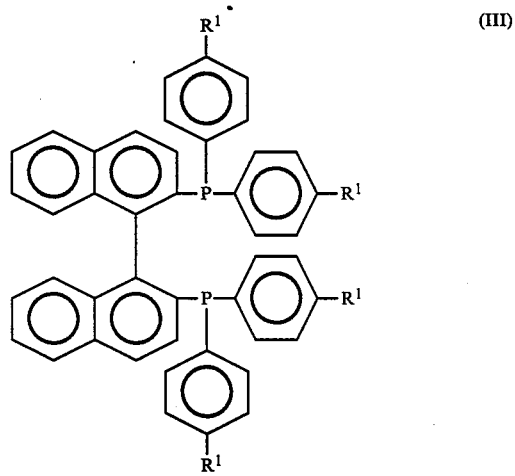

wherein
R$^1$ represents a hydrogen atom, a methyl group, or a t-butyl group;
R$^2$ represents a lower alkyl group or a trifluoromethyl group; and X is as defined above, as a catalyst at a temperature of from 70° to 150° C. to obtain an optically active alcohol represented by formula (VI):

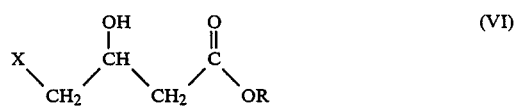

wherein X and R are as defined above, and then reacting the optically active alcohol as obtained with trimethylamine without isolation, is disclosed.

2 Claims, No Drawings

PROCESS FOR PREPARING CARNITINE

FIELD OF THE INVENTION

This invention relates to a process for preparing vitamin $B_T$, i.e., carnitine, useful for treating digestive paracrisis or other purposes. More particularly, it relates to a process for preparing carnitine from an optically active alcohol obtained by asymmetric hydrogenation of a γ-halogeno-β-keto ester in the presence of a ruthenium-optically active phosphine complex.

BACKGROUND OF THE INVENTION

Known techniques for asymmetrically synthesizing optically active alcohols useful as intermediates of pharmaceuticals, liquid crystal materials, and the like include a process comprising asymmetric hydrogenation using baker's yeast and a process comprising asymmetric hydrogenation using a specific catalyst.

In particular, with respect to asymmetric hydrogenation of β-ketonic acid derivatives to obtain optically active alcohols, it has been reported that the asymmetric hydrogenation can be carried out by using a rhodium-optically active phosphine complex as a catalyst. For example, J. Solodar reports in Chemtech., 421–423 (1975) that asymmetric hydrogenation of methyl acetoacetate gives methyl 3-hydroxybutyrate in an optical yield of 71% ee.

Further, asymmetric hydrogenation using a tartaric acid-modified nickel catalyst has been proposed. According to this technique, asymmetric hydrogenation of methyl acetoacetate gives methyl 3-hydroxybutyrate in an optical yield of 85% ee as disclosed in Tai, Yukagaku, 822–831 (1980).

On the other hand, considerable literature exists on the preparation of carnitine. For example, known processes for preparing carnitine include a process comprising reacting epichlorohydrin with prussic acid and trimethylamine to obtain cartinonitrile and hydrolyzing the resulting cartinonitrile as disclosed in E. Strack et al., Chem. Ber., Vol. 86, 525 (1953); a process comprising reacting a 4-chloro-3-hydroxybutyric acid alkyl ester with a trialkylamine as disclosed in JP-B-37-5172 (the term "JP-B" as used herein means an "examined published Japanese patent application"); a process comprising reacting a diketene compound with chlorine, reacting the product with an optically active amino acid methyl ester to obtain an optically active amino acid amide as a diastereomer as disclosed in JP-A-61-271261 (the term "JP-A" as used herein means an "unexamined published Japanese patent application"); and a process comprising reducing an ethyl γ-chloroacetoacetate with baker's yeast to obtain optically active ethyl 3-hydroxybutyrate and reacting the product with trimethylamine as disclosed in J. Am. Chem. Soc., Vol. 105, 5925–5926 (1983).

In preparing optically active alcohols, although the process using baker's yeast produces an alcohol having relatively high optical purity, the resulting optically active alcohol is limited in absolute configuration, and synthesis of an enantiomer is difficult.

The process utilizing asymmetric hydrogenation of β-ketonic acid derivatives in the presence of a rhodium-optically active phosphine complex does not produce an alcohol having sufficient optical purity. Besides, metallic rhodium to be used in the catalyst is expensive due to limitations in place and quantity of production. When used as a catalyst component, it forms a large proportion of the cost of the catalyst, ultimately resulting an increase in cost of the final commercial products.

The process using a tartaric acid-modified nickel catalyst involves disadvantages of difficulty in preparing the catalyst and insufficient optical yield.

In general, recovery of an active substance by optical resolution is not economical because it requires an optically active substance in an amount equimolar to a substrate and the undesired enantiomer is useless or should be subjected to racemization for re-resolution.

The asymmetric hydrogenation using baker's yeast essentially involves separation of the produced optically active substance from the yeast.

SUMMARY OF THE INVENTION

As a result of extensive investigations with the purpose of settling the above-described problems, the inventors have found that a γ-halogeno-β-keto ester can be asymmetrically hydrogenated in a short reaction time by using a relatively cheap ruthenium-optically active phosphine complex as a catalyst and conducting the reaction at temperatures higher than those conventionally employed to thereby obtain an optically active alcohol having a high optical purity and that carnitine can be obtained by starting with the resulting optically active alcohol without isolation. The present invention has been completed based on these findings.

The present invention relates to a process for preparing carnitine which comprises asymmetrically hydrogenating a γ-halogeno-β-keto ester represented by formula (I):

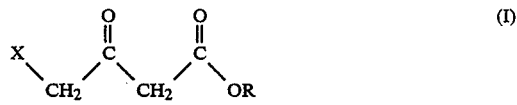

wherein X represents a chlorine atom or a bromine atom; and R represents a lower alkyl group, in the presence of a ruthenium-optically active phosphine complex represented by formula (II), (III) or (IV):

(II)

(IV)

(V)

wherein L represents 2,2'-bis(di-p-$R^1$-phenylphosphino)-1,1'-binaphthyl of formula (III):

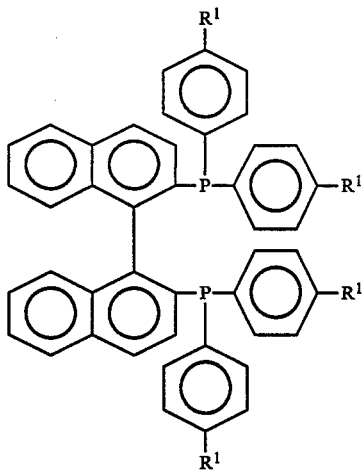

wherein
R¹ represents a hydrogen atom, a methyl group, or a t-butyl group;
R² represents a lower alkyl group or a trifluoromethyl group; and X is as defined above,
as a catalyst at a temperature of from 70° to 150° C. to obtain an optically active alcohol represented by formula (VI):

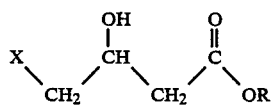

wherein X and R are as defined above, and then reacting the optically active alcohol as obtained without isolation with trimethylamine.

DETAILED DESCRIPTION OF THE INVENTION

In the foregoing formulae, the lower alkyl group for R and R² preferably contains from 1 to 4 carbon atoms. Specific examples thereof include a methyl group, an ethyl group, a propyl group, an isopropyl group, an n-butyl group, and a t-butyl group.

The γ-halogeno-β-keto ester represented by formula (I) which can be used in the present invention as a starting compound specifically includes methyl 4-chloroacetoacetate, ethyl 4-chloroacetoacetate, isopropyl 4-chloroacetoacetate, butyl 4-chloroacetoacetate, t-butyl 4-chloroacetoacetate, methyl 4-bromoacetoacetate, ethyl 4-bromoacetoacetate, isopropyl 4-bromoacetoacetate, butyl 4-bromoacetoacetate, and t-butyl 4-bromoacetoacetate.

Of the ruthenium-optically active phosphine complexes to be used as a catalyst, those represented by formula (II) can be obtained by the process disclosed in T. Ikariya et al., *J. Chem. Soc., Chem. Commun.,* 922–924 (1985) and JP-A-61-63690. That is, the compound of formula (II) can be obtained by reacting ruthenium chloride and cycloocta-1,5-diene (hereinafter referred to as COD) in an ethanol solution to obtain [RuCl₂(COD)]ₙ, and reacting 1 mole of [RuCl₂(COD)]ₙ with 1.2 moles of a 2,2′-bis(di-p-R¹-phenylphosphino)-1,1′-binaphthyl (a compound represented by L) in a solvent, e.g., toluene or ethanol, in the presence of 4 moles of triethylamine while heating.

The complex represented by formula (IV) can be obtained by the process disclosed in JP-A-62-265293. That is, the compound of formula (IV) wherein R2 is a lower alkyl group can be obtained by reacting the above-described complex of formula (II) with a carboxylic acid salt in an alcohol solvent, e.g., methanol, ethanol, t-butanol, etc., removing the solvent by distillation, and extracting the residue with a solvent, e.g., diethyl ether, ethanol, etc. The compound of formula (IV) wherein R² is a trifluoromethyl group can be obtained by reacting the thus prepared Ru(OCOCH₃)₂(L) with trifluoroacetic acid in methylene chloride.

The complex represented by formula (V) can be obtained by the process described in D. G. Lynn et al., *J. Am. Chem. Soc.,* Vol. 109, 5856–5858 (1987), in which Ru(OCOCH₃)₂(L) and hydrogen chloride or hydrogen bromide are reacted in a molar ratio of 1:2 in methanol and the solvent is removed by distillation under reduced pressure.

Specific examples of the above-described ruthenium-phosphine complexes according to the present invention are shown below. In the following formulae, the phosphine derivative moiety includes the respective enantiomers, though not shown.

Ru₂Cl₄(BINAP)₂(C₂H₅)₃N
 [BINAP represents 2,2′-bis(diphenylphosphino)-1,1′-dinaphthyl]
Ru₂Cl₄(T-BINAP)₂(C₂H₅)₃N
 [T-BINAP represents 2,2′-bis(di-p-tolylphosphino)-1,1′-binaphthyl]
Ru₂Cl₄(t-Bu-BINAP)₂(C₂H₅)₃N
 (t-Bu-BINAP represents 2,2′-bis(di-p-t-butylphenylphosphino)-1,1′-binaphthyl]
Ru(OCOCH₃)₂(BINAP)
Ru(OCOCH₃)₂(T-BINAP)
Ru(OCOCH₃)₂(t-Bu-BINAP)
Ru(OCOCF₃)₂(BINAP)
Ru(OCOCF₃)₂(T-BINAP)
Ru(OCOCF₃)₂(t-Bu-BINAP)
RuCl₂(BINAP)
RuCl₂(T-BINAP)
RuBr₂(BINAP)
RuBr₂(t-Bu-BINAP)

In carrying out the present invention, a γ-halogeno-β-keto ester of formula (II) is dissolved in an amphiprotic solvent, e.g., methanol, ethanol, isopropanol, etc., or a mixed solvent of the amphiprotic solvent and tetrahydrofuran, methylene chloride, toluene, etc. The solution is charged in an autoclave, and from 1/5,000 to 1/20,000 mole of a ruthenium-optically active phosphine complex is added thereto per mole of the γ-halogeno-β-keto ester (I). The hydrogenation reaction is effected under stirring at a temperature of from 70° to 150° C., preferably from 90° to 120° C., at a hydrogen pressure of from 5 to 100 kg/cm² for a period of from about 5 to 50 minutes. After completion of the reaction, the solvent is removed by distillation, and the residue is subjected to distillation under reduced pressure or isolation by silica gel column chromatography to obtain an optically active alcohol of formula (VI) in a substantially quantitative yield.

After the solvent removal, trimethylamine is added to the product, followed by heating under stirring. After removing any unreacted trimethylamine by distillation, a hydrochloric acid aqueous solution is added to the residue to form carnitine hydrochloride. Water is distilled off, and ethanol is added to the residue to obtain crude crystals, which are then purified.

The present invention is now illustrated in greater detail with reference to Examples and Comparative Example, but it should be understood that the present invention is not deemed to be limited thereto. In these examples, analytical instruments and conditions used for various analyses are as follows.

(1) Gas Chromatography (GC):
SHIMADZU GC-9A manufactured by Shimadzu Corporation
Column: OV 101 Silica Capillary, 0.25 mm in diameter and 25 m in length, manufactured by Gasukuro Kogyo Inc.
Measurement Temperature: 100° to 250° C. and increasing at a rate of 3° C./min.

(2) High-Performance Liquid Chromatography (HPLC):
Hitachi Liquid Chromatography 665A-11 manufactured by Hitachi, Ltd.
Column: Chemcopak Nucleosil 100-3, 4.6 mm in diameter and 300 mm in length, manufactured by Chemco Co.
Developing Solvent: Hexane:diethyl ether=7:3; flow rate: 1 ml/min.
Detector: UV Detector 635M (UV-254), manufactured by Hitachi, Ltd.

(3) Optical Rotation:
Polarimeter DIP-4, manufactured by Japan Spectroscopic Co., Ltd.

(4) $^1$H NMR Spectrum
Bruker-AM 400 (400 MHz), manufactured by Bruker Co.
Chemical shift was determined by using tetramethylsilane as an internal standard.

EXAMPLE 1

Synthesis of L-Carnitine

In a 200 ml-volume stainless steel autoclave whose atmosphere had been replaced with nitrogen were charged 31 g (0.2 mole) of methyl 4-chloroacetoacetate and 60 ml of methanol. To the mixture was added 168 mg (0.2 mmole) of Ru(OCOCH$_3$)$_2$((−)-BINAP), and the mixture was heated to 100° C. When the temperature reached 100° C., 100 kg/cm$^2$ of hydrogen was introduced to the autoclave. The hydrogenation reaction completed in 15 minutes. After confirming disappearance of the starting material by gas chromatography, the methanol was removed by distillation. To the residue was added 150 ml of a 27 wt % aqueous solution of trimethylamine, followed by stirring at 70° C. for 1.5 hours and then at 90° C. for 30 minutes. Any unreacted trimethylamine was removed from the reaction mixture by distillation, and to the residue was added 15% by weight of a hydrochloric acid aqueous solution. The water was removed by distillation under reduced pressure, and ethanol was added to the residue to obtain 40 g of crude crystals of L-carnitine hydrochloride. Recrystallization from ethanol-acetone gave 18.1 g (46%) of L-carnitine hydrochloride having a melting point of 142° C. Optical Rotation: $[\alpha]^{23}$ −23° (c=4, H$_2$O).

Next, some examples for synthesis of the intermediate optically active alcohol are given by reference to the following Examples 2 to 11. The optically active alcohols obtained in these Examples 2 to 11 can be derived into L-carnitine upon being reacted with trimethylamine in a similar manner to that in Example 1.

EXAMPLE 2

Synthesis of Ethyl (3R)-(+)-4-Chloro-3-hydroxybutyrate

In a 200 ml-volume stainless steel-made autoclave whose atmosphere had been replaced with nitrogen were charged 8.23 g (50 mmoles) of ethyl 4-chloroacetoacetate and 20 ml of ethanol. To the mixture was added 84 mg (0.05 mmole) of Ru$_2$Cl$_4$((−)-BINAP)$_2$(C$_2$H$_5$)$_3$N, and the mixture was heated to 100° C. When the temperature reached 100° C., 100 kg/cm$^2$ of hydrogen was introduced into the autoclave, and the mixture was stirred under heating. After cooling to room temperature, the reaction mixture was taken out, and the ethanol was removed by distillation. Distillation of the residue gave 8.07 g (97) of ethyl 4-chloro-3-hydroxybutyrate having a boiling point of 74°–75° C./1 mmHg).

Optical Rotation: $[\alpha]_D^{21}$ +20.9° (c=7.71, CHCL$_3$).

$^1$HNMR (CDCl$_3$) ppm: 1.28 (t, 3H, J=7, 3 Hz), 2.55–2.70 (m, 2H), 3.17 (brd, 1H, J=4.9 Hz), 3.55–3.65 (m, 2H), 4.18 (q, 2H, J=7.3 Hz), 4.20–4.30 (m, 1H).

The resulting product was esterified with (R)α-methoxy-α-trifluoromethylphenylacetyl chloride, and the ester was analyzed by HPLC. From the area ratio of the chromatogram, the optical yield of the product was found to be 97.2% ee.

EXAMPLES 3 TO 11

Various optically active alcohols were prepared in the same manner as in Example 2, except for changing the substrate, catalyst and reaction conditions as shown in Table 1 below. The yield and optical yield of the resulting products are also shown in Table 1.

COMPARATIVE EXAMPLE 1

The procedure of Example 2 was repeated, except for using RuBr$_2$((+)-BINAP) as a catalyst and conducting the reaction at 19° C. for 16 hours. The reaction results are shown in Table 1.

TABLE 1

Substrate: X-CH₂-C(=O)-CH₂-C(=O)-OR

Product: X-CH₂-CH(OH)-CH₂-C(=O)-OR

| Example No. | X | R | Catalyst | Substrate/catalyst Molar Ratio | Hydrogen Pressure (kg/cm²) | Temp. (°C.) | Time (min) | Yield (%) | Optical Yield (% ee) |
|---|---|---|---|---|---|---|---|---|---|
| 3 | Cl | Et* | RuBr₂((−)—BINAP) | 1300 | 100 | 100 | 7 | 97.3 | 97.0 |
| 4 | Br | Et | RuBr₂((+)—T—BINAP) | 1300 | 100 | 100 | 10 | 80.0 | 93.0 |
| 5 | Cl | i-pr** | Ru₂Cl₄((+)—T—BINAP) | 1000 | 70 | 110 | 20 | 93.0 | 95.0 |
| 6 | Cl | Et | Ru₂Cl₄((+)—BINAP)₂(Et)₃N | 1180 | 100 | 100 | 10 | 97.0 | 96.0 |
| 7 | Cl | Et | Ru(OCOCF₃)₂((−)—BINAP) | 2000 | 100 | 95 | 15 | 97.8 | 93.0 |
| 8 | Cl | t-Bu*** | Ru₂Cl₄((−)—t-Bu—BINAP)₂(Et)₃N | 1000 | 100 | 100 | 20 | 95.0 | 92.0 |
| 9 | Cl | Et | Ru(OCOCH₃)₂((−)—BINAP) | 1000 | 100 | 100 | 10 | 98.0 | 96.0 |
| 10 | Cl | Et | RuCl₂((−)—T—BINAP) | 5000 | 100 | 110 | 20 | 97.5 | 91.0 |
| 11 | Cl | Me**** | Ru₂Cl₂((−)—T—BINAP) | 10000 | 100 | 100 | 25 | 98.0 | 92.0 |
| Comparative Example 1 | Cl | Et | RuBr₂((+)—BINAP) | 1300 | 98 | 19 | 16 hrs. | 47.0 | 67.0 |

Note:
Et*: ethyl group
i-pr**: isopropyl group
t-Bu***: t-butyl group
Me****: methyl group According to the present invention, optically active alcohols having high optical purity useful as intermediates for pharmaceuticals, can be prepared at satisfactory efficiency by asymmetrically hydrogenating γ-halogeno-β-keto esters using a cheap ruthenium-optically active phosphine complex at a relatively high temperature in a short period of time. The thus prepared optically active alcohol can be subjected to the reaction with trimethylamine without isolation to prepare carnitine, an important drug.

While the invention has been described in detail and with reference to specific embodiments thereof, it will be apparent, to one skilled in the art that various changes and modifications can be made therein without departing from the spirit and scope thereof.

What is claimed is:

1. A process for preparing carnitine which comprises asymmetrically hydrogenating a γ-halogeno-β-keto ester represented by formula (I):

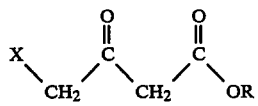

wherein X represents a chlorine atom or a bromine atom; and R represents a lower alkyl group, in the presence of a ruthenium-optically active phosphine complex represented by formula (II), (III) or (IV):

$Ru_2Cl_4(L)_2(C_2H_5)_3N$      (II)

$Ru(OCOR^2)_2(L)$      (IV)

$RuX_2(L)$      (V)

wherein L represents 2,2'-bis(di-p-$R^1$-phenylphosphino)-1,1'-binaphthyl of formula (III):

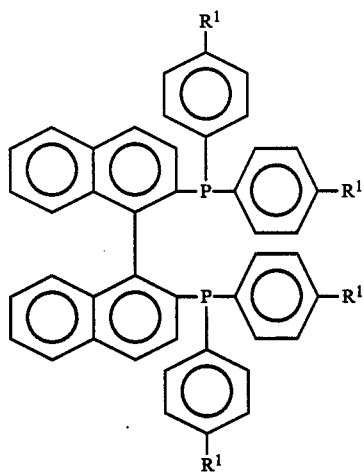

wherein
  $R^1$ represents a hydrogen atom, a methyl group, or a t-butyl group;
  $R^2$ represents a lower alkyl group or a trifluoromethyl group; and X is as defined above,
as a catalyst at a temperature of from 70° to 150° C. to obtain an optically active alcohol represented by formula (VI):

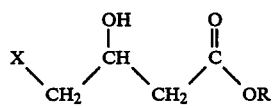

wherein X and R are as defined above, and then reacting the optically active alcohol as obtained with trimethylamine without isolation.

2. A process as claimed in claim 1, wherein said asymmetric hydrogenation is carried out at a temperature of from 90° to 120° C.

* * * * *